US 8,597,691 B2
Dec. 3, 2013

(12) United States Patent
Satou et al.

(54) ANTI-HYPOTHERMIA COMPOSITION

(75) Inventors: Kazunori Satou, Shizuoka (JP);
Takashi Ogawa, Shizuoka (JP); Saori Mori, Shizuoka (JP)

(73) Assignee: Ajinomoto Co., Inc., Tokyo (JP)

( * ) Notice: Subject to any disclaimer, the term of this patent is extended or adjusted under 35 U.S.C. 154(b) by 83 days.

(21) Appl. No.: 12/581,428

(22) Filed: Oct. 19, 2009

(65) Prior Publication Data
US 2010/0080858 A1  Apr. 1, 2010

Related U.S. Application Data

(63) Continuation of application No. PCT/JP2008/057467, filed on Apr. 17, 2008.

(30) Foreign Application Priority Data

Apr. 20, 2007  (JP) ................. 2007-111895

(51) Int. Cl.
*A01N 59/00* (2006.01)
*A61K 33/00* (2006.01)
(52) U.S. Cl.
USPC .......................................... 424/717; 424/600
(58) Field of Classification Search
None
See application file for complete search history.

(56) References Cited

U.S. PATENT DOCUMENTS

| | | | | |
|---|---|---|---|---|
| 4,876,205 A | * | 10/1989 | Green et al. | 436/66 |
| 4,975,281 A | * | 12/1990 | Harwood et al. | 424/441 |
| 2005/0100615 A1 | * | 5/2005 | Yamazaki | 424/677 |
| 2006/0063839 A1 | * | 3/2006 | Ogawa et al. | 514/561 |
| 2009/0131338 A1 | | 5/2009 | Satou et al. | |

FOREIGN PATENT DOCUMENTS

| | | |
|---|---|---|
| EP | 1 618 878 A1 | 1/2006 |
| JP | 2002-338495 | 11/2002 |
| JP | 2007-55992 | 3/2007 |
| WO | WO 2004/096207 A1 | 11/2004 |

OTHER PUBLICATIONS

Alfaro et al., 'Components of the blood acid-base disturbance that accompanies urethane anaesthesia in rats during normothermia and hypothermia', Clinical and Experimental Pharmacology and Physiology, 1997, vol. 24, pp. 498-502.*

Morriss, W.H.,'The Prophylaxis of anesthesia acidosis' JAMA, the Journal of the American Medical Association, 1917, vol. 68, pp. 1391-1394.*

Gupta et al. "Comparison of Recovery Profile After Ambulatory Anesthesia with Propofol, Isoflurane, Sevoflurane and Desflurane: A Systematic Review" (2004) Anesth Analg, vol. 98, pp. 632-641.*

David J. Dula, MD, "Use of IV Bicarbonate in Hypothermia" JACEP, vol. 48, XP002574682, Jan. 1979, p. 79.

John D. Evans, et al., "Metabolism of Rabbit Bone Marrow in Vitro in Ringer-Bicarbonate Medium Containing No Added Glucose", The Journal of Biological Chemistry, vol. 177, No. 1, XP002574683, Jul. 12, 1949, pp. 357-365.

* cited by examiner

*Primary Examiner* — James H Alstrum Acevedo
*Assistant Examiner* — Daniel L Branson
(74) *Attorney, Agent, or Firm* — Oblon, Spivak, McClelland, Maier & Neustadt, L.L.P.

(57) ABSTRACT

An anti-hypothermia composition is provided, in particular an anti-hypothermia composition that prevents hypothermia caused by general anesthesia during surgical operations. The composition prevents hypothermia by preventing the decrease in the biological function of patients and correcting acidosis. Specifically, the anti-hypothermia composition is a preparation containing a bicarbonate ion and provided in the form of an infusion fluid. The infusion fluid preferably contains sodium bicarbonate as a major component that serves as a source of the bicarbonate ion, along with each or a combination of other electrolytes, glucose and amino acids.

10 Claims, 1 Drawing Sheet

ANTI-HYPOTHERMIA COMPOSITION

CONTINUING APPLICATION INFORMATION

The present application is a continuation of International application No. PCT/JP2008/057467, filed on Apr. 17, 2000, and claims benefit to Japanese patent application No. JP 2007-111895, filed on Apr. 20, 2007, both of which are incorporated herein by reference.

FIELD OF THE INVENTION

The present invention relates to an anti-hypothermia composition and, in particular, to an anti-hypothermia composition for preventing hypothermia caused by general anesthesia during surgical operations.

BACKGROUND OF THE INTENTION

Human body temperature is normally maintained at about 37° C. However, the body temperature decreases when the function of the central nervous system (and, thus, the temperature regulatory center) is decreased by general anesthesia performed during surgical operations. The result is often hypothermia.

Hypothermia causes complications including chillness/discomfort, shivering, tachycardia/ischemic change in ECG, delayed emergence, wound infection, delayed healing of wounds, decreased immune activity and blood coagulation disorder.

Hypothermia ultimately leads to delayed postoperative recovery and decreased immune activity, increasing the risk of complications. Also, hypothermia during anesthesia is one of the factors that cause delayed awakening from anesthesia. For these reasons, prevention of hypothermia during surgical operations is medically important.

To prevent this type of hypothermia, various measures are taken in medical fields to keep patients warm during surgical operations, including aluminum heat-insulating materials, heat circulatory mats, warmed infusion fluids and heating with warm air streams. However, conventional heat circulatory mats can only warm part of a patient's body depending on the body position of the patient and thus have limited effectiveness in keeping patients warm. Heating with warm air streams is effective but costly since it requires warming covers, which cover patients, and other supplies.

Furthermore, any of the conventional approaches for keeping patients warm takes long to raise the body temperature back to normal levels once the body temperature has decreased beyond the threshold below which the temperature center can no longer return the body temperature to the normal levels.

Several recent studies have reported that a total amino acid infusion fluid preparation containing high concentrations of amino acids (total amino acid concentration=10 w/v % or higher) are effective in preventing hypothermia (Non-Patent Documents 1 to 3). An anti-hypothermia composition containing amino acids has also been proposed (Patent Document 1).

In the course of our studies of postoperative awakening from anesthesia, the present inventors have found that awakening from anesthesia is accelerated in patients receiving a perioperative infusion fluid containing a bicarbonate ion during the perioperative (intraoperative) period, as compared to patients receiving a perioperative infusion fluid containing sodium acetate or sodium lactate. Based on this finding, the present inventors have proposed an anesthesia arousal composition that contains a bicarbonate ion as an electrolyte (Patent Document 2).

The present inventors conducted studies to examine the relationship between acidosis and the time it takes for patients to awaken from anesthesia using a rat model with partial liver excision as well as a rat model of streptozotocin (STZ)-induced diabetic ketoacidosis. The present inventors also conducted studies to examine the ability of bicarbonated-Ringer's solution to facilitate recovery (awakening time) after anesthesia using a rat model with partial kidney excision. These studies have revealed that the time to awakening from anesthesia is significantly shorter in patients receiving the bicarbonated-Ringer's solution as compared to patients receiving the acetated-Ringer's solution or the lactated-Ringer's solution.

One reason for this is believed to be that the changes in the plasma concentration of an anesthetic and thus, the rate at which the anesthetic is metabolized by the liver, differ depending on the type of Ringer's solution. It has been suggested that this difference results from the difference in the ability of each Ringer's solution to correct acidosis. Another reason for the accelerated awakening time is believed to be the difference in the protein binding of propofol among the different Ringer's solutions.

Thus, the bicarbonated-Ringer's solution that contains sodium bicarbonate rather than sodium acetate or sodium lactate (alkalizers used in the conventional Ringer's solution) can directly correct acidosis since its alkalization effect does not involve the metabolic pathway of sodium acetate or sodium lactate.

According to the study conducted by the present inventors to examine the time to awakening from anesthesia in animal models of different metabolic diseases, the time to awakening from anesthesia is inversely related to the blood pH: the more severe acidosis is, the more delayed the emergence from anesthesia will be. This observation suggests that quick correction of acidosis accelerates awakening of patients from anesthesia, thus facilitating the postoperative recovery of the patients.

It has been observed that patients receiving the bicarbonated-Ringer's solution during the surgery have less risk of developing hypothermia than those receiving other types of extracellular fluid replacement (for example, acetated-Ringer's solution).

The present inventors hypothesized that the reduced risk of hypothermia in patients administered the bicarbonated-Ringer's solution was due to the ability of the bicarbonated-Ringer's solution to correct acidosis and to prevent the decrease in the biological function. To verify this hypothesis, the present inventors conducted a study using a normal rat model and a rat model of STZ-induced diabetic ketoacidosis to determine whether or not the bicarbonated-Ringer's solution is more effective in the prevention of hypothermia during anesthesia than the acetated-Ringer's solution or the official Ringer's solution (prepared according to Japanese Pharmacopoeia) and, if so, to what degree.

The study showed that, in normal rats, the body temperature remained at the same level in the bicarbonated-Ringer group and in the acetated-Ringer group. The body temperature of these two groups showed a tendency to be higher than that of the Ringer group, though no significant differences were observed between the two groups and the Ringer group.

Normal rats generally develop hypothermia, but not acidosis, when put under anesthesia Also, none of the studied official Ringer's solution, the bicarbonated-Ringer's solution and the acetated-Ringer's solution contained any components that serve as an energy source (carbohydrate, amino acids and fats).

Since the bicarbonated-Ringer's solution and the acetated-Ringer's solution have electrolyte compositions more close to physiological state than the official Ringer's solution, the bicarbonated-Ringer's solution and the acetated-Ringer's solution are more effective in maintaining circulatory kinetics and homeostasis than the official Ringer's solution.

In normal rats, these differences are considered to be the cause of the difference in the degree of hypothermia between the group receiving the bicarbonated-Ringer's solution or the acetated-Ringer's solution and the group receiving the official Ringer's solution.

In diabetic rats, the body temperature remained higher in the bicarbonated-Ringer group than in the acetated-Ringer group and official Ringer group. Also, the change in the body temperature before the termination of anesthetic was significantly smaller in the bicarbonated-Ringer group than in the acetated-Ringer group and the official Ringer group.

Diabetic rats generally develop significant acidosis with a blood pH of 7.2 (ketoacidosis). As reported in the non-patent document 4, in ketoacidosis, the alkalization effect of sodium acetate becomes less significant because the metabolism of ketone bodies produced in large quantities in ketoacidosis interferes with the metabolism of sodium acetate.

Unlike sodium acetate, an alkalizer used in the acetate-Ringer's solution, sodium bicarbonate used as an alkalizer in the bicarbonated-Ringer's solution can supply bicarbonate ion without being involved in the metabolism. Thus, it can be used as an effective alkalizer in patients with metabolic disorder and organ dysfunction to correct acidosis and maintain a high blood pH that is difficult to achieve by the use of the other Ringer's solutions.

In summary, the studies conducted by the present inventors have proven that the difference in the degree of hypothermia among the groups administered the bicarbonated-Ringer's solution, the acetated-Ringer's solution and the official Ringer's solution is mainly due to the fact that the ability of a Ringer's solution to prevent hypothermia varies depending on whether or not an alkalizer is present in the Ringer's solution, or, if it is present, the type of the alkalizer.

Since the bicarbonated-Ringer's solution and the acetate-Ringer's solution have compositions more close to physiological state than the official Ringer's solution, these solutions can suppress the decrease in the biological function caused by anesthesia and, thus, the resulting hypothermia. This is an advantage that cannot be achieved by the administration of the official Ringer's solution. The bicarbonated-Ringer's solution, which can provide alkalization effect without requiring the metabolism, can bring about the alkalization effect faster than the acetated-Ringer's solution. For this reason, the bicarbonated-Ringer's solution can correct acidosis faster than the acetated-Ringer's solution in patients with diseases associated with acidosis. As a result, the decreased biological function due to acidosis can recover quickly, which helps keep the body temperature high.

The present invention has been devised based on the foregoing knowledge.

Patent Document 1: International Patent Publication No. WO2004/096267

Patent Document 2: PCT/JP 2006/310671

Non-Patent Document 1: *Anesh. Analg.* 89: 1551-1556, 1999

Non-Patent Document 2: *Japanese Journal of Surgical Metabolism and Nutrition* 36(4): 215-220, 2002

Non-Patent Document 3: *British J. of Anaesthesia* 90: 58-61, 2003

Non-Patent Document 4: *Pharmaceutical Regulatory Science* 28(9): 664-672, 1997

SUMMARY OF THE INVENTION

Accordingly, it is an object of the present invention to provide an anti-hypothermia composition, in particular an anti-hypothermia composition that can prevent hypothermia caused by general anesthesia during surgical operations by preventing the decrease in the biological function of patients and correcting acidosis during surgical operations.

Thus, the present invention in one aspect concerns the following:

(1) an anti-hypothermia composition containing a bicarbonate ion;

(2) the anti-hypothermia composition according to (1) above, wherein the bicarbonate ion is contained as an electrolyte;

(3) the anti-hypothermia composition according to (1) or (2) above, containing sodium bicarbonate as a major component that serves as a source of the bicarbonate ion, along with each or a combination of another electrolyte, glucose and an amino acid;

(4) the anti-hypothermia composition according to (1), (2) or (3) above, provided in the form of Ringer's solution;

(5) the anti-hypothermia composition according to any of (1) to (4) above, configured to prevent or ameliorate perioperative complications;

(6) the anti-hypothermia composition according to any of (1) to (4) above, configured to facilitate recovery from surgical invasion;

(7) the anti-hypothermia composition according to any of (1) to (4) above, configured to be administered before the onset of hypothermia or before the beginning of anesthesia; and (8) an anti-hypothermia composition that contains a bicarbonate ion and acts by preventing decrease in biological function of patients or correcting acidosis in patients.

The anti-hypothermia composition provided by the present invention is essentially an infusion fluid containing a bicarbonate ion. More specifically, it is an infusion fluid that contains sodium bicarbonate as a major component that serves as a source of the bicarbonate ion (electrolyte). The anti-hypothermia composition serves to prevent the decrease in the biological function of patients and quickly correct acidosis, thus maintaining normal or near-normal blood and tissue pH. This in turn helps maintain the body temperature high, thus providing a significant advantage.

The anti-hypothermia composition facilitates the recovery of the metabolic function by accelerating the recovery of the biological function of patients. It thus allows tissues and organs to quickly resume their normal function. As a result, increased risk of complications caused by the delayed action of body's protective mechanism or decreased immune activity can be avoided.

DETAILED DESCRIPTION OF THE INVENTION

Figure 1:
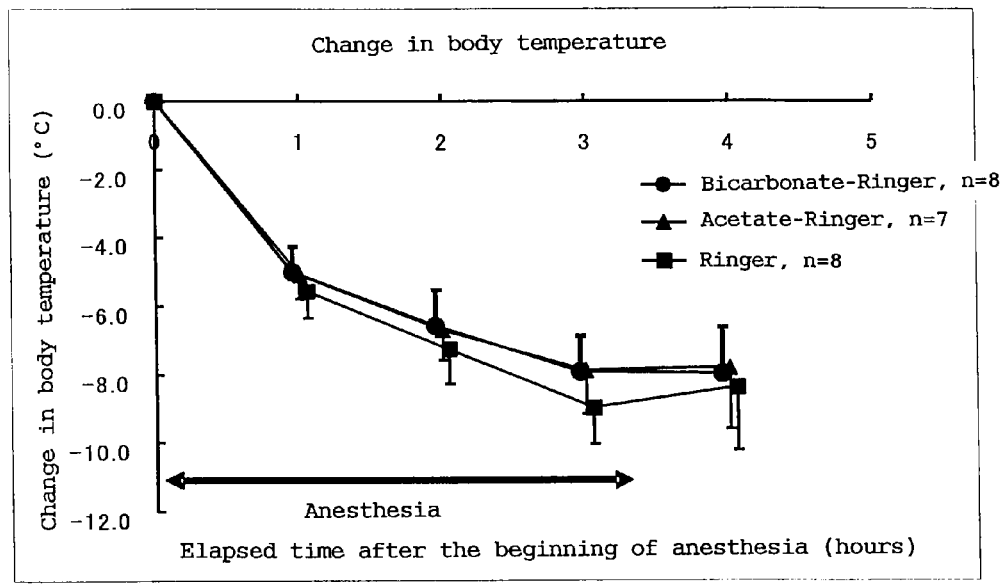
FIG. 1 is a diagram showing the changes in body temperature in three groups of normal rats administered a Ringer's solution of the present invention, an acetate-Ringer's solution as a control and an official Ringer's solution as a control, respectively.

As described above, the anti-hypothermia composition provided by the present invention contains a bicarbonate ion that acts to quickly correct acidosis. More specifically, it is a preparation, preferably an infusion fluid, that contains sodium bicarbonate, a major component that serves as a source of bicarbonate ion (electrolyte), along with each or a combination of another electrolyte, glucose and an amino acid. The anti-hypothermia composition is provided in the form of a Ringer's solution, a maintenance solution, a starting solution, a solution for correction of dehydration, or a solution for postoperative recovery, in particular in the form of a Ringer's solution.

When the anti-hypothermia composition of the present invention containing a bicarbonate ion is provided in the form of a Ringer's solution, a type of infusion fluid used to replace the extracellular fluid, it contains a bicarbonate ion preferably at a concentration of 20 to 40 mEq/L and more preferably at a concentration of 22 to 30 mEq/L. Preferably, it also contains other electrolytes: 130 to 145 mEq/L of sodium ion; 2 to 5 mEq/L of potassium ion; 90 to 130 mEq/L of chlorine ion; 2 to 5 mEq/L of calcium ion; 0.5 to 2.5 mEq/L of magnesium ion; and 0 to 7 mEq/L citrate ion, along with 0 to 5 g/L of glucose.

When the anti-hypothermia composition of the present invention containing a bicarbonate ion is provided in the form of a maintenance solution, another type of infusion fluid, it contains a bicarbonate ion preferably at a concentration of 15 to 30 mEq/L and more preferably at a concentration of 18 to 25 mEq/L. Preferably, it also contains other electrolytes: 30 to 40 mEq/L of sodium ion; 15 to 25 mEq/L of potassium ion; and 30 to 40 mEq/L of chlorine ion, along with 40 to 80 g/L of glucose.

When the anti-hypothermia composition of the present invention containing a bicarbonate ion is provided in the form of a starting solution, a solution for correction of dehydration, or a solution for postoperative recovery, it contains a bicarbonate ion and electrolytes at concentrations suitable for its intended use.

When the composition is intended as a starting solution, it preferably contains 30 to 90 mEq/L of sodium ion, 35 to 80 mEq/L of chlorine ion, 20 to 30 mEq/L of bicarbonate ion and 25 to 40 g/L of glucose. When it is intended as a solution for correction of dehydration, it preferably contains 60 to 90 mEq/L of sodium ion, 20 to 30 mEq/L of potassium ion, 0 to 5 mEq/L of magnesium ion, 45 to 70 mEq/L of chlorine ion, 5 to 10 mmol/L of phosphorus, 20 to 50 mEq/L of bicarbonate ion and 10 to 35 g/L of glucose. When it is intended as a solution for postoperative recovery, it preferably contains 30 mEq/L of sodium ion, 5 to 10 mEq/L of potassium ion, 20 to 30 mEq/L of chlorine ion, 10 to 20 mEq/L of bicarbonate ion and 30 to 50 L glucose. Thus, the concentration of bicarbonate ion in the composition may range from 15 to 90 mEq/L.

Any electrolytes may be used suitable for the intended use. Examples thereof include sodium chloride, sodium citrate, sodium acetate, sodium lactate, sodium dihydrogen phosphate, disodium hydrogen phosphate, sodium gluconate, sodium glycerophosphate, sodium malate, potassium chloride, dibasic potassium phosphate, potassium acetate, potassium citrate, potassium lactate, potassium glycerophosphate, potassium malate, calcium chloride, calcium lactate, calcium gluconate, calcium glycerophosphate, dibasic calcium phosphate, calcium malate, magnesium chloride, magnesium gluconate and magnesium glycerophosphate.

Of these components, sodium chloride, potassium chloride, calcium chloride, magnesium chloride, sodium bicarbonate, sodium citrate and glucose are particularly preferred.

The anti-hypothermia composition of the present invention containing a bicarbonate ion is intended for use as an infusion fluid. However, a stable preparation containing sodium bicarbonate ion is difficult to prepare since sodium bicarbonate that serves as a source of the bicarbonate ion, an important base required to maintain the acid-base balance of extracellular fluid, tends to react with calcium and magnesium to form insoluble calcium carbonate and magnesium carbonate, and since an aqueous sodium bicarbonate solution, when left or heated, produces carbon dioxide that increases the pH of the solution. For this reason, the infusion fluid of the present invention containing a bicarbonate ion may be prepared either upon use, or as separate solutions of sodium bicarbonate and an electrolyte, which may be contained in a two separate chambers of a container. For convenience of use, a single solution-type preparation is preferred.

Although the anti-hypothermia composition of the present invention containing a bicarbonate ion may be applied to any symptom or disease condition to prevent hypothermia of patients, it is particularly effective in preventing hypothermia caused by anesthesia. Anesthesia is generally classified into two types: general anesthesia and local anesthesia. General anesthesia includes inhalation anesthesia induced by isoflurane, sevoflurane and other gases that have analgesic, sedative and hypnotic effects (laughter gas) and intravenous anesthesia induced by propofol and other intravenous anesthetics. Local anesthesia includes tetracaine, lidocaine and dibucaine. The anti-hypothermia composition of the present invention containing a bicarbonate ion is particularly effective in the prevention of hypothermia caused by, of the different types of anesthesia, general anesthesia performed during surgical operations.

The anti-hypothermia composition of the present invention containing a bicarbonate ion for use as an infusion fluid is a stable preparation that can be administered to patients who have their biological functions decreased by acidosis or other similar conditions to quickly correct acidosis, thus facilitating the recovery of their biological functions and preventing hypothermia. The anti-hypothermia composition of the present invention containing a bicarbonate ion can correct acidosis faster than other infusion fluids containing sodium acetate or sodium lactate. When used during surgical operations in which patients are put under general anesthesia, the composition also facilitates awakening of patients from anesthesia by quickly recovering biological functions and correcting acidosis.

Since the anti-hypothermia composition of the present invention has particularly high ability to correct acidosis, it helps maintain normal or near-normal blood pH, so that the decreased biological function can recover quickly and the emergence from anesthesia can be facilitated.

Thus, the anti-hypothermia composition of the present invention can prevent and/or ameliorate complications associated with hypothermia and can facilitate recovery of patients from surgical invasion.

EXAMPLES

The present invention will now be described with reference to the following examples.

Example 1

Storage Stability

Ringer's solutions containing 20.0, 22.5, 25.0, 27.5 and 30.0 mEq/L of bicarbonate ion ($HCO_3^-$) were prepared.

Specifically, the infusion preparations were prepared according to the formulations shown in Table 1 below. For each preparation, the components were dissolved in water to make a 10 L solution (measured pH=8.0). Carbon dioxide was bubbled through the solution to adjust the pH to 6.5. The solution was then filtered and loaded in a 500 mL glass vial. The vial was autoclaved at 115° C. for 15 min. In this manner, five different Ringer's solutions containing 20.0, 22.5, 25.0, 27.5 and 30.0 mEq/L of bicarbonate ion ($HCO_3^-$) were prepared.

TABLE 1

| Components (g) | Bicarbonate ion concentration (mEq/L) | | | | |
|---|---|---|---|---|---|
| | 20.0 | 22.5 | 25.0 | 27.5 | 30.0 |
| Sodium chloride | 64.3 | 62.8 | 61.4 | 59.9 | 58.4 |
| Potassium chloride | 2.98 | 2.98 | 2.98 | 2.98 | 2.98 |
| Calcium chloride dihydrate | 2.21 | 2.21 | 2.21 | 2.21 | 2.21 |
| Magnesium chloride hexahydrate | 1.02 | 1.02 | 1.02 | 1.02 | 1.02 |
| Sodium bicarbonate | 16.8 | 18.9 | 21.0 | 23.1 | 25.2 |
| Sodium citrate dihydrate | 4.90 | 4.90 | 4.90 | 4.90 | 4.90 |

At the beginning and after a three-month storage period at room temperature, the infusion fluids (Ringer's solutions) were analyzed for pH, insoluble material, insoluble particle count, amounts of components and carbon dioxide concentration in the vial space. The results are shown in Tables 2 and 3 below. As can be seen from the results, each of the Ringer's solutions of the present invention did not undergo any significant changes during the storage period. Each solution proved to be a stable infusion fluid that did not decompose or form precipitation during the storage period.

TABLE 2

| | | Bicarbonate ion concentration (mEq/L) | | | | | |
|---|---|---|---|---|---|---|---|
| | | 20.0 | | 22.5 | | 25.0 | |
| | | Initial | 3M | Initial | 3M | Initial | 3M |
| pH | | 7.2 | 7.1 | 7.1 | 7.2 | 7.1 | 7.1 |
| Insoluble material test | | ND | ND | ND | ND | ND | ND |
| Insoluble particles (particles/mL or less) | 10 μM> | 0.0 | 0.5 | 0.1 | 0.9 | 0.0 | 0.4 |
| | 22 μM> | 0.0 | 0.0 | 0.0 | 0.0 | 0.0 | 0.0 |
| Contents (w/v %) | Na | 0.302 | 0.302 | 0.304 | 0.303 | 0.303 | 0.303 |
| | K | 0.015 | 0.015 | 0.015 | 0.015 | 0.015 | 0.015 |
| | Ca | 0.00582 | 0.00584 | 0.00582 | 0.00586 | 0.00583 | 0.00587 |
| | Mg | 0.00114 | 0.00115 | 0.00116 | 0.00111 | 0.00116 | 0.00112 |
| | Chlorine | 0.4168 | 0.4144 | 0.4081 | 0.4065 | 0.4001 | 0.3974 |
| | Bicarbonate | 0.119 | 0.116 | 0.134 | 0.132 | 0.149 | 0.149 |
| | Citric acid | 0.0309 | 0.0318 | 0.0310 | 0.0319 | 0.0309 | 0.0320 |
| Space ($CO_2$ %) | | 7.16 | 9.85 | 5.40 | 9.53 | 6.10 | 10.24 |

ND: Not detected

TABLE 3

| | | Bicarbonate ion concentration (mEq/L) | | | |
|---|---|---|---|---|---|
| | | 27.5 | | 30.0 | |
| | | Initial | 3M | Initial | 3M |
| pH | | 7.2 | 7.1 | 7.1 | 7.2 |
| Insoluble material test | | ND | ND | ND | ND |
| Insoluble particles (particles/mL or less) | 10 μM> | 0.0 | 0.2 | 0.0 | 0.1 |
| | 22 μM> | 0.0 | 0.0 | 0.0 | 0.0 |
| Contents (w/v %) | Na | 0.302 | 0.305 | 0.304 | 0.306 |
| | K | 0.015 | 0.015 | 0.015 | 0.015 |
| | Ca | 0.00586 | 0.00589 | 0.00594 | 0.00592 |
| | Mg | 0.00116 | 0.00113 | 0.00115 | 0.00114 |
| | Chlorine | 0.3932 | 0.3984 | 0.3865 | 0.3830 |
| | Bicarbonate | 0.163 | 0.165 | 0.183 | 0.178 |
| | Citric acid | 0.0310 | 0.0322 | 0.0312 | 0.0322 |
| Space ($CO_2$ %) | | 8.02 | 10.42 | 10.14 | 11.90 |

ND: Not detected

Example 2

Anti-Hypothermia Effect

[Method]

7-week-old male SD rats and STZ-induced diabetic ketoacidosis rats were used.

(1) Preparation of STZ-Induced Diabetic Ketoacidosis Rats

STZ was dissolved in 0.1 M citrate buffer to form an aqueous STZ solution. This solution was administered to rats from the tail vein at a dose of 100 mg/kg/mL. After 48 hours, the blood gas was measured to confirm the onset of acidosis.

(2) Insertion of Drug Delivery Catheter

The subject rats (normal rats and STZ-induced diabetic ketoacidosis rats) were anesthetized with sodium pentobarbital (NENBUTAL; Dainippon Sumitomo Pharma Co., Ltd.) and shaved on the right side of the neck and in the upper dorsal region (around scapula). The shaved regions were sterilized with ISODINE solution (Meiji Seika Kaisha Ltd.) and a catheter was inserted from the right external jugular vein to the origin of the right upper vena cava according to the method described by Steiger et al (Arch. Surg., 104: 330-332, 1972). After placement of the catheter, the animals were kept warm until awakening from anesthesia using a thermal mat. The animals were then returned to the cage and kept until the test.

(3) Test for the Anti-Hypothermia Effect

Normal rats and STZ-induced diabetic ketoacidosis rats were infused with the bicarbonate-Ringer's solution of the present invention or an acetate-Ringer's solution or an official Ringer's solution as controls. Each solution was continuously administered via the catheter placed in the origin of the right upper vena cava at a rate of 20 mL/kg/hr. 1 hour after the beginning of the administration of the solutions, an anesthetic (propofol) was started and continued for 3 hours (introduced at 15 mg/kg, and maintained at 45 mg/kg for the first one hour and at 33.75 mg/kg for the subsequent 2 hours).

The body temperature was measured at the beginning of infusion fluid, 1 and 2 hours after the beginning of anesthetic, at the termination of anesthetic, and 1 hour after the termination of anesthetic.

The Ringer's solution of the present invention, and the acetate-Ringer's solution and the official Ringer's solution as controls were prepared according to the compositions shown in Table 5 below and tested as infusion fluids.

The groups tested were as shown in Table 4.

TABLE 4

| | Alkalizer | Number of cases | |
|---|---|---|---|
| | | Normal rats | STZ rats |
| Ringer's solution of the present invention | Sodium bicarbonate | 8 | 10 |
| Acetate-Ringer's solution | Sodium acetate | 8 | 10 |
| Official Ringer's solution | — | 8 | — |

TABLE 5

| | Composition (Unit: mEq/L) | | |
|---|---|---|---|
| Components | Ringer's solution of the present invention | Acetate-Ringer's solution | Official Ringer's solution |
| $Na^+$ | 135 | 130 | 147 |
| $K^+$ | 4 | 4 | 4 |
| $Ca^{2+}$ | 3 | 3 | 4.5 |
| $Mg^{2+}$ | 1 | — | — |
| $Cl^-$ | 113 | 109 | 155.5 |
| $HCO_3^-$ | 25 | — | — |
| $acetate^-$ | — | 28 | — |
| $citrate^{3-}$ | 5 | — | — |

[Results]

The body temperature was measured by a rectal thermometer for small animals (TAKARA THERMISTOR D613; Takara Kogyo Co., Ltd.).

Figure 2:
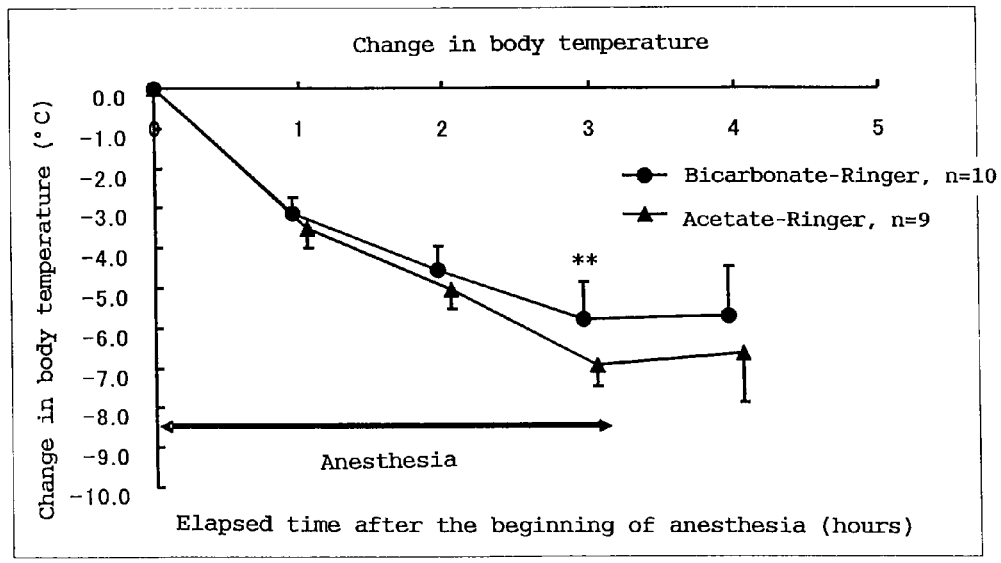
FIG. 2 is a diagram showing the changes in body temperature in the two groups of STZ-induced diabetic ketoacidosis rats administered the Ringer's solution of the present invention and the acetate-Ringer's solution as a control, respectively.

The results are shown in FIGS. 1 and 2.

FIG. 1 is a diagram showing the changes in body temperature in the three groups of normal rats administered the Ringer's solution of the present invention, the acetate-Ringer's solution as a control and the official Ringer's solution as a control, respectively. FIG. 2 is a diagram showing the changes in body temperature in the two groups of STZ-induced diabetic ketoacidosis rats administered the Ringer's solution of the present invention and the acetate-Ringer's solution as a control, respectively.

In normal rats, the body temperature remained higher in the Ringer group according to the present invention than in the official Ringer group. The body temperature of the Ringer group according to the present invention was substantially the same as the body temperature of the acetate-Ringer group serving as the control at each time point (FIG. 1).

In STZ-induced diabetic ketoacidosis rats, the body temperature of the Ringer group according to the present invention showed a tendency to be higher than the body temperature of the acetate Ringer group (FIG. 2).

In STZ-induced diabetic ketoacidosis rats, the decrease in the body temperature ($\Delta° C.$) of the Ringer group according to the present invention over the course of the anesthetic administration period was significantly smaller than that of the acetate-Ringer group.

Specifically, the decrease was −5.8° C. for the Ringer group according to the present invention and −6.9° C. for the acetate-Ringer group ($p<0.05$).

These results demonstrate that, while the anti-hypothermia composition of the present invention containing a bicarbonate ion exhibits a similar anti-hypothermia effect to the acetate-Ringer's solution in normal rats, it shows higher anti-hypothermia effect than the acetate-Ringer's solution of the control when used in STZ-induced diabetic ketoacidosis rats.

This observation suggests that the effect of the anti-hypothermia composition of the present invention containing a bicarbonate ion results from its ability to prevent the decrease in the biological function and quickly correct acidosis. Thus, the anti-hypothermia composition of the present invention containing a bicarbonate ion has proven to be useful in surgical operations involving general anesthesia, in particular in maintaining the body temperature of patients with metabolic acidosis during surgery.

INDUSTRIAL APPLICABILITY

As set forth, the anti-hypothermia composition of the present invention contains a bicarbonate ion as an essential component and serves to maintain normal or near-normal blood and tissue pH by preventing the decrease in the body function of patients and quickly correcting acidosis. Thus, the anti-hypothermia composition of the present invention helps keep the body temperature of patients high.

The prompt recovery of the biological function due to the prevention of hypothermia facilitates the recovery of metabolic function and allows tissues and organs to resume their normal function quickly. As a result, increased risk of complication caused by the delayed action of body's protective mechanism or decreased immune activity can be avoided. The anti-hypothermia composition of the present invention is of significant medial importance in that it prevents hypothermia caused by general anesthesia during surgical operations.

The invention claimed is:

1. A method of ameliorating hypothermia in a patient receiving propofol, comprising administering to the patient an effective amount Bicarbonate-Ringer's solution.

2. The method of claim 1, wherein the Bicarbonated-Ringer's solution does not contain amino acids.

3. The method of claim 1, wherein the concentration of the bicarbonate ion in the solution is 20 to 40 mEq/L.

4. The method of claim 1, wherein the concentration of the bicarbonate ion in the solution is 22 to 30 mEq/L.

5. The method of claim 1, wherein the patient is undergoing a surgical procedure.

6. The method of claim 1, wherein administering the solution also corrects acidosis in the patient.

7. The method of claim 1, wherein the solution contains 130-145 mEq/L of sodium ion, 2-5 mEq/L of potassium ion, 90-130 mEq/L of chloride ion, 2-5 mEq/L of calcium ion, 0.5-2.5 mEq/L of magnesium ion, 0-7 mEq/L of citrate ion and 0-5 g/L of glucose.

8. The method of claim 1, wherein the solution comprises sodium bicarbonate as a major component that serves as a source of the bicarbonate ion, along with one or more other electrolytes and/or glucose.

9. The method of claim 8, wherein said other electrolyte(s) comprises One or more of sodium chloride, sodium citrate, sodium acetate, sodium lactate, sodium dihydrogen phosphate, disodium hydrogen phosphate, sodium gluconate, sodium glycerophosphate, sodium malate, potassium chloride, dibasic potassium phosphate, potassium acetate, potassium citrate, potassium lactate, potassium glycerophosphate, potassium malate, calcium chloride, calcium lactate, calcium gluconate, calcium glycerophosphate, dibasic calcium phosphate, calcium malate, magnesium chloride, magnesium gluconate, and magnesium glycerophosphate.

10. The method of claim 9, the solution contains one or more of sodium chloride, potassium chloride, calcium chloride, magnesium chloride, sodium citrate and glucose.

\* \* \* \* \*